United States Patent [19]

Takagaki et al.

[11] Patent Number: 4,874,855
[45] Date of Patent: Oct. 17, 1989

[54] STEROID COMPOUNDS AND PROCESS OF PREPARING THE SAME

[75] Inventors: Hidetsugu Takagaki, Sakura; Masayoshi Abe, Chiba; Michihiro Watanabe, Ichihara; Kazuyuki Takeuchi, Sodegaura; Shigenori Nakanishi, Chiba; Yuuko Nakata, Tomakomai; Keiji Yamazaki, Sakura, all of Japan

[73] Assignee: Dainippon Ink and Chemicals, Inc., Tokyo, Japan

[21] Appl. No.: 189,849

[22] Filed: May 3, 1988

[30] Foreign Application Priority Data

Nov. 4, 1987 [JP] Japan .................... 62-278931

[51] Int. Cl.⁴ ............................................. C07J 1/00
[52] U.S. Cl. .................................. 540/3; 260/397.47
[58] Field of Search ..................... 540/3; 260/347.47

[56] References Cited

U.S. PATENT DOCUMENTS 4,226,862 10/1980 Riva et al. .................... 514/174
4,525,303 6/1985 Takagaki et al. ............... 540/26

OTHER PUBLICATIONS

Chemical Abstracts; vol. 87 (1977); #102538v; Gaffuri.

Primary Examiner—Douglas W. Robinson
Assistant Examiner—Joseph A. Lipovsky
Attorney, Agent, or Firm—Oblon, Spivak, McClelland, Maier & Neustadt

[57] ABSTRACT

Disclosed are steroid compounds represented by general formula (I)

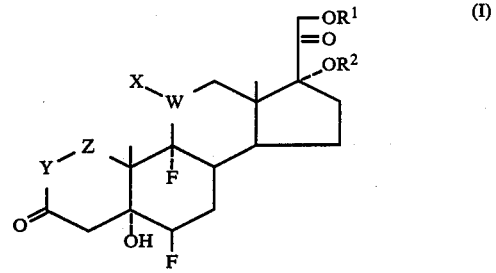

wherein X and W together as >W-X represent a carbonyl group (>C=O) or a hydroxymethylene group (>CH(OH)), the hydroxy moiety of the hydroxymethylene group being of β-arrangement, and OR¹ and OR² independently represent an ester residue, and Y and Z together as —Y—Z— represent a —(PpSe)-CH—CH₂— group where Pp represent a phenyl group or a 2-pyridyl group, or Y and Z each represent an ethenylene group or a 1-bromoethylene group.

Also disclosed is a process of preparing the compound (I) includes reacting 6β, 9α-difluoro-5α,17α,21-trihydroxypregna-3,11,20-trione-17,21-diesters or 6β,9α-difluoro-5α,11β,17α,21-tetrahydroxypregna-3,20-dione-17,21-diesters as starting compound with an organic selenenyl halide selected from the group consisting of 2-pyridylselenenyl chloride, 2-pyridylselenenyl bromide, phenylselenenyl chlolride and phenylselenenyl bromide.

Further disclosed is a process of preparing 2-bromo-6β,9α-difluoro-11β,17α,21-trihydroxy-1,4-pregnadien-3,20-di-one-17,21-diester represented by general formula (VII)

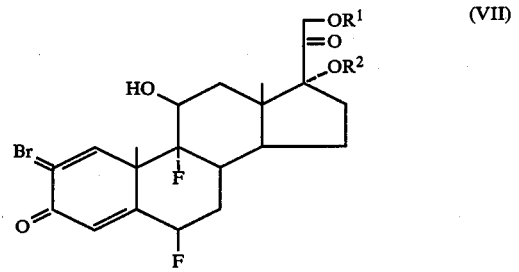

wherein OR¹ and OR² independently represent an ester residue, which comprises reacting with hydrogen chloride, or with thionyl chloride in the presence of a basic substance, the compound (V), and optionally reducing with a reducing agent when >W-X represents a carbonyl group.

17 Claims, No Drawings

STEROID COMPOUNDS AND PROCESS OF PREPARING THE SAME

FIELD OF THE INVENTION

This invention relates to new process of preparing steroid compounds and intermediate compounds as well as process of preparing same.

BACKGROUND OF THE INVENTION

Many investigations on steroid compounds have heretofore been made, and some steroid compounds are known to have pharmaceutical activity. Especially, 2-bromo-6β,9α-difluoro-11β,17α,21-trihydroxy-1,4-pregnadien-3,20-dione-17,21-diester (hereinafter referred to as compound VII) are known to be good medicine. U.S. Pat. No. 4,226,862 describes that the compound VII has valuable pharmaceutical activity such as anti-inflammatory activity or anti-rheumarthritic activity, and that the compound VII rarely has side effects, such as decrease in body weight, accumulation of sodium, decrease in potassium, or suppression of adrenal glands and hypophysis, which would often be observed with various conventional steroids having physiological activity. Also, the other investigation reported that the compound VII can be administered by intra-articulational injection and thus it is an effective anti-rheumatic agent.

European Pat. No. 97328 and U.S. Pat. No. 4,525,303 disclose a method of preparing the compound VII using hydrocortisone-21-ester which is readily available as a starting compound. This method comprises the steps of; (1) dehydration of a hydroxy group at the 11-position of the starting compound, (2) acetylation of a hydroxy group at the 17-position, (3) bromhydrination at the 11-position, (4) epoxidation at the 11-position with a base, (5) cleavage of the epoxy compound with hydrogen fluoride, (6) oxidation of the hydroxy group at the 11-position, (7) ketalation, (8) reduction of the hydroxy group at the 11-position, (9) epoxidation of the double bond between the 5-position and the 6-position with a peracid, (10) cleavage of the epoxy compound with hydrogen fluoride. In this method, 6β,9α-difluoro-5α,17α,21-trihydroxypregna-3,11,20-trione-17,21-diesters or 6β,9α-difluoro-5α,11β,17α,21-tetrahydroxypregna-3,20-dione-17,21-diesters can be synthesized from the starting compound above and then the compound VII can be prepared from the diesters above by the following steps; (11) dibromination at the 2-position of the diesters, (12) dehydrobromination and dehydration in an amide solvent in the presence of a metal halide at high temperature.

In step (11), dibromide compound can be obtained through monobromide compound, when the diesters and a large amount of bromine are reacted at high temperature for a short period time. However, on the occasion of scaling up, the dibromide compound cannot be prepared stably with high quality and yield, because a great deal of bromine cannot be poured quickly into the reaction system, and because the dibromide compound in which the bromine has been transferred from the 2-position to the 4-position is produced as impurity in the dibromination. Therefore, the above method is found disadvantageous in that the compound VII cannot be produced stably with high quality and yield, because the completion of reaction in step (12) depends on the purity of the dibromide compound produced in step (11), and because the dibromide compound tends to be decomposed with hydrogen bromide and water produced as impurity since the reaction proceeds at high temperature in step (12). The above method, also, has a problem of taking much time to purify the crude compound VII.

The above method is inadequate for preparing the compound 10 on an industrial scale or on the occasion of scaling up.

SUMMARY OF THE INVENTION

With view to obviating the above-described defects and developing an efficient process of preparing useful physiologically active steroid compounds, intensive investigation has been made and as a result it has now been found that some organic selenium-containing steroid compounds are useful for the purpose.

Therefore, this invention provides a process of preparing 2-bromo-6β,9α-difluoro-11β,17α,21-trihydroxy-1,4-pregnadien-3,20-dione-17,21-diester represented by general formula (VII)

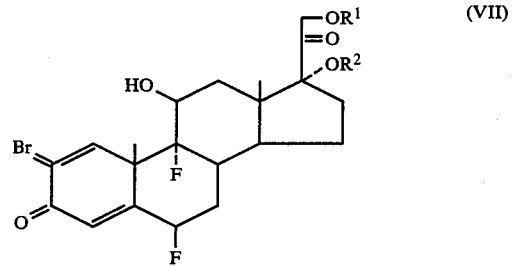

wherein $OR^1$ and $OR^2$ independently represent an ester residue, which comprises reacting with hydrogen chloride, or with thionyl chloride in the presence of a basic substance, a compound represented by general formula (I)

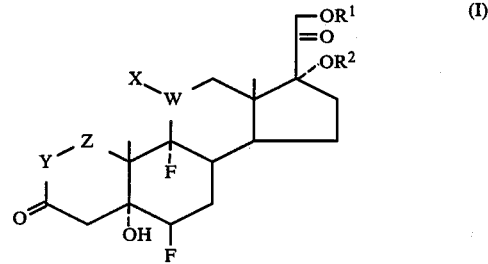

wherein X and W together as >W—X represent a carbonyl group (>C=O) or a gydroxymethylene group (>CH(OH)), the hydroxy moiety of the gydroxymethylene group being of β-arrangement, and $OR^1$ and $OR^2$ have the same meanings as defined above, and optionally reducing the resulting compound with a reducing agent when >W—X represents a carbonyl group.

In another aspect, this invention provides a compound represented by general formula (I)

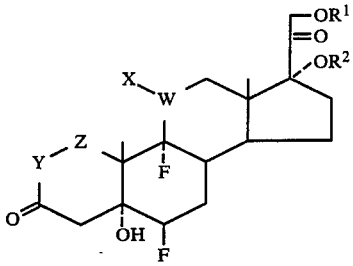

(I)

wherein Y and Z together as —Y—Z— represent a —(PpSe)CH—CH$_2$— group where Pp represents a phenyl group or a 2-pyridyl group, or Y and Z each represent an ethenylene (or vinylene) group or a 1-bromoethenylene (or bromovinylene) group; and W, X, OR$^1$ and OR$^2$ have the same meanings as defined above.

In further aspect, this invention provides a process of preparing a compound of formula (I), which comprises reacting 6β,9α-difluoro-5α,17α,21-trihydroxypregna-3,11,20-trione-17,21-diesters or 6β,9α-difluoro-5α,11β,17α,21-tetrahydroxypregna-3,20-dione-17,21-diesters as a starting compound with an organic selenenyl halide selected from the group consisting of 2-pyridylselenenyl chloride, 2-pyridylselenenyl bromide, phenylselenenyl chloride and phenylselenenyl bromide.

DETAILED DESCRIPTION OF THE INVENTION

The compounds (I) of the present invention are useful as an intermediate for producing 6β,9α-difluorocorticoids which has pharmacological activity and are important as an intermediate for producing the aforesaid compound VII. In the general formula (I), the ester residue is an acyloxy group, a sulfuric ester group or a phosphoric ester group. The sulfuric ester group and phosphoric ester group are derived from sulfuric acid and phosphoric acid, respectively. The acyloxy groups represented by OR$^1$ and OR$^2$ generally contain 1 to 20 carbon atoms, preferably 1 to 16 carbon atoms, and examples thereof include a formyloxy group, an acetoxy group, a malonyloxy group, a benzoyloxy group, a cinnamoyloxy group, etc. Organic acids such as aliphatic carboxylic acids, alicyclic carboxylic acids, aromatic carboxylic acids, arylaliphatic carboxylic acids, heterocyclic carboxylic acids, thiocarboxylic acids, amino carboxylic acids can be used as an acid which constitutes the acyloxy group represented by OR$^1$ or OR$^2$. Preferably, the carboxylic acids include formic acid, acetic acid, chloroacetic acid, trifluoroacetic acid, propionic acid, butyric acid, valeric acid, trimethylacetic acid, diethylacetic acid, caproic acid, crotonic acid, enanthic acid, caprylic acid, palmitic acid, undecanoic acid, undecylenic acid, oxalic acid, succinic acid, glutaric acid, pimelic acid, tartaric acid, maleic acid, lactic acid, carbamic acid, glycine, alkoxylcarboxylic acids, hexahydrobenzoic acid, cyclopentylpropionic acid, cyclohexylacetic acid, cyclohexylbutyric acid, benzoic acid, phthalic acid, phenylacetic acid, phenylpropionic acid, furan-2-carboxylic acid, nicotinic acid and isonicotinic acid. More preferably, the carboxylic acids include acetic acid, trimethylacetic acid, propionic acid, β-phenylpropionic acid, α-phenylpropionic acid, valeric acid, dicarboxylic acids such as succinic acid. The sulfonic acids preferably include methanesulfonic acid and toluenesulfonic acid. The above acyloxy groups represented by OR$^1$ are formed preferably by the carboxylic acids because the ester group at the 21-position in the general formula (I) has superior biological activity. Also, the OR$^1$ represents preferably polycarboxylic esters, water-soluble salts thereof or inorganic acids which can be converted into the water-soluble salts.

The compounds of this invention can be prepared according to the following reaction schemes.

REACTION SCHEME 1

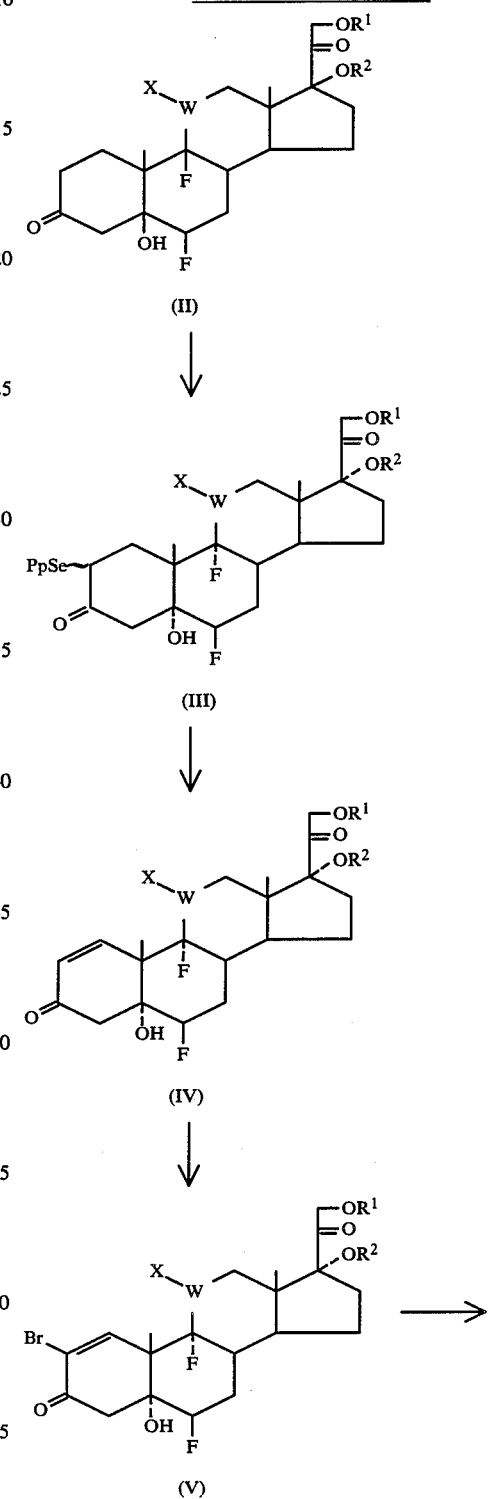

-continued
REACTION SCHEME 1

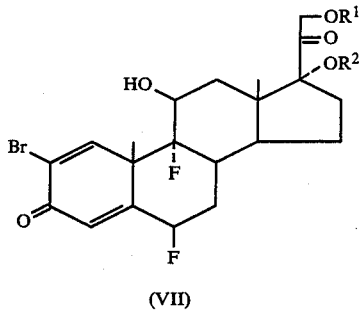

That is, a steroid compound represented by the general formula (II) above is reacted with an organic selenenyl halide selected from the group consisting of 2-pyridylselenenyl chloride, 2-pyridylselenenyl bromide, phenylselenenyl chloride and phenylselenenyl bromide in an organic solvent at a temperature preferably from 0° C. to 50° C. to form compound represented by the general formula (III) above. Then, the compound represented by the general formula (III) is oxidized with an oxidizing agent in an organic solvent at a temperature preferably from −50° C. to +30° C. to obtain a compound represented by the general formula (IV) above. The compound (IV) is brominated with bromine in an organic solvent inert to bromine at a temperature preferably from −40° C. to +50° C. to form a compound represented by the general formula (V) above. The compound (V) is then reacted with thionyl chloride, or with thionyl chloride in the presence of a basic compound, at a temperature preferably from −30° C. to +50° C. to form a compound represented by the general formula (VII) when the compound (V) contains a hydroxymethylene group of β-arrangement at the 11-position, i.e., when >W—X represents a hydroxymethylene group of β-arrangement. On the other hand, when the compound (V) contains a carbonyl group at the 11-position, i.e., >W—X represents a >C=O group, the compound (V) is reduced with a reducing agent in an organic solvent at a temperature of preferably from −80° C. to +60° C.

REACTION SCHEME 2

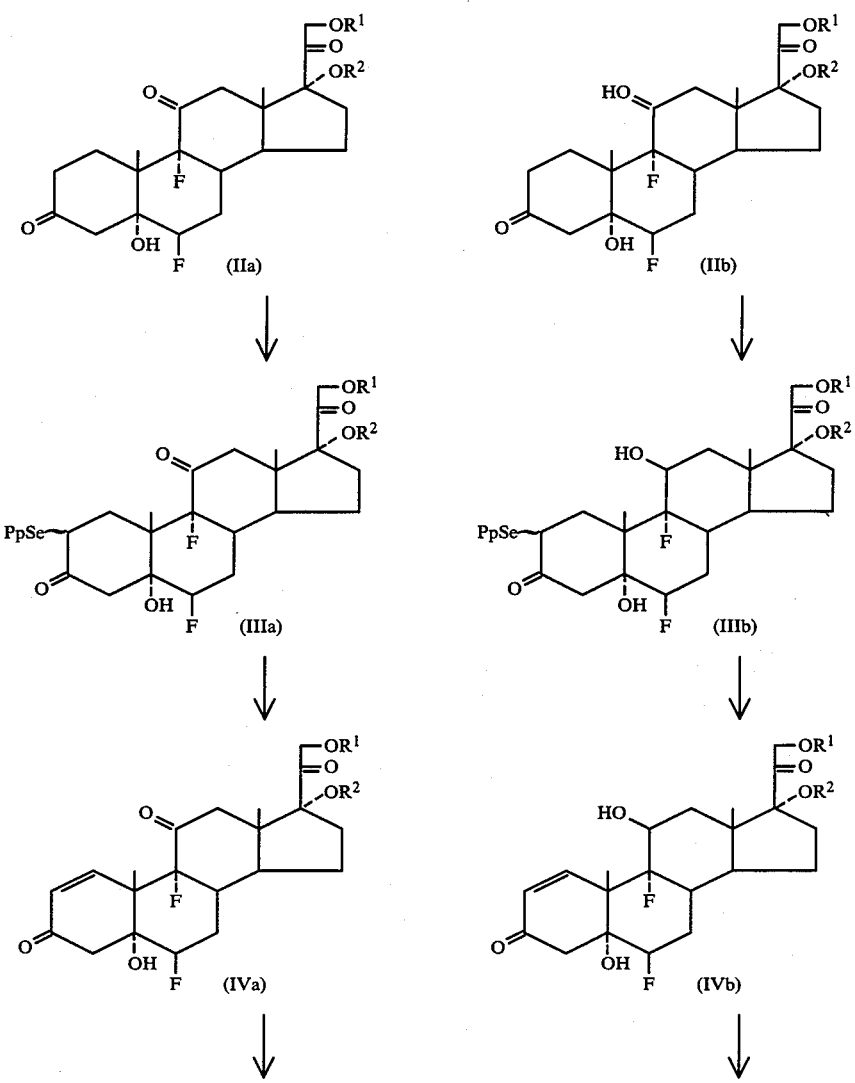

-continued
REACTION SCHEME 2

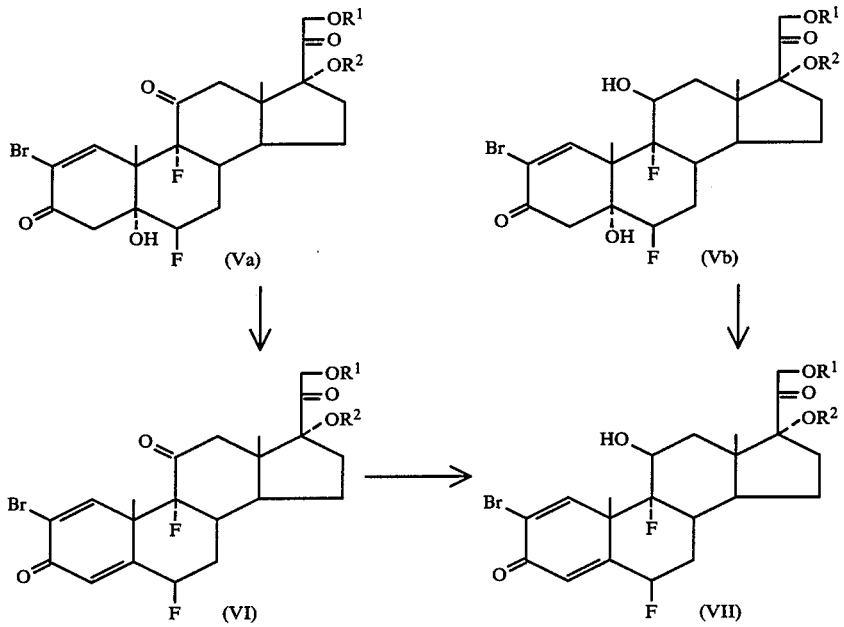

In the above formulae, the symbol ~ at the 2-position indicates that the group attached to the 2-position may be α- or β-arrangement or a mixture of such α- and β-isomers can be used.

The process of preparing steroid compounds according to this invention will be described more specifically.

For example, of the compounds of this invention represented by the general formula (I), those compounds in which $R^1$ and $R^2$ each represent an acetyl group can be prepared using the compound of the general formula (IIa) as a starting compound by the following procedure. In this case, the starting compound is 6β,9α-difluoro-5α,17β,21-trihydroxypregna-3,11,20-trione-17,21-diacetate (Compound IIa).

Preparation Step 1

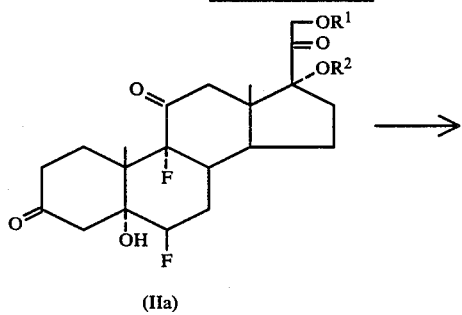

-continued
Preparation Step 1

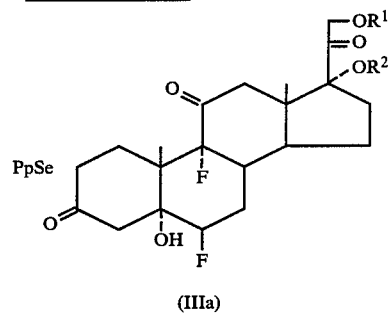

In the above formulae, Pp represents a 2-pyridyl group, and $R^1$ and $R^2$ have the same meanings as defined above.

In the reaction, the compound (IIa) and 2-pyridylselenenyl chloride or 2-pyridylselenenyl bromide are reacted in an organic solvent (e.g., halogenated hydrocarbons such as methylene chloride, chloroform, dichloroethane, ethers such as tetrahydrofuran, dioxane, esters such as ethyl acetate, methyl acetate, amides such as dimethylformaldehyde, N-methylpyrrolidone) at a temperature depending on the solvent used, preferably from 0° C. to 50° C., to form the compound of general formula (IIIa) of this invention. The compound (IIIa) represents 6β,9α-difluoro-2-(2-pyridylseleno)-5α,1-7α,21-tri-hydroxypregna-3,11,20-trione-17,21-diacetate. In the above reaction, phenylselenenyl chloride or phenylselenenyl bromide can be used instead of 2-pyridylselenenyl chloride or 2-pyridylselenenyl bromide. In the case, the compound (IIa) is reacted with triethylamide and trimethylsilane chloride in nitriles such as acetonitrile in the presence of zinc chloride anhydrolide, and then the product is reacted with phenylselenenyl chloride or phenylselenenyl bromide. Also, the compound (II) can be reacted directly with phenylselenenyl chloride in a solvent such as ethyl acetate. The thus-obtained compound of this invention represents 6β,9α-difluoro-2-phenylseleno-5α,17α,21-trihydroxypregna-3,11,20-tri-one-17,21-diacetate.

Preparation Step 2

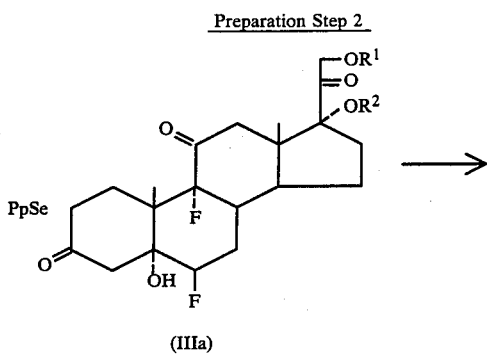

In the above formulae, $R^1$, $R^2$ and Pp have the same meanings as defined above.

The compound (IIIa) and an oxidizing agent (e.g., hydrogen peroxide, metachloroperbenzoic acid, sodium periodate, peracetic acid, ozone, N-bromosuccinimide, N-chlorosuccinimide) are reacted in an organic solvent (e.g., halogenated hydrocarbons such as methylene chloride, chloroform, dichloroethane, alcohols such as methanol, ethanol, esters such as ethyl acetate, methyl acetate, and acids such as acetic acid) at a temperature depending on the solvent and the oxidizing agent used, preferably from $-50°$ C. to $+30°$ C., to form the compound of general formula (IVa). The compound (IVa) of this invention represents 6β,9α-difluoro-5α,17α,21-trihydroxy-1-pregnen-3,11,20-trione-17,21-diacetate.

Preparation Step 3

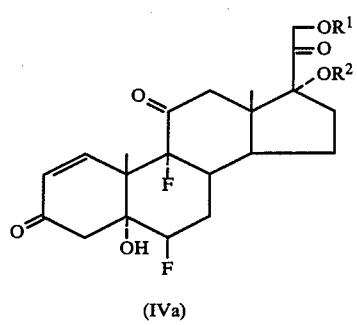

-continued
Preparation Step 3

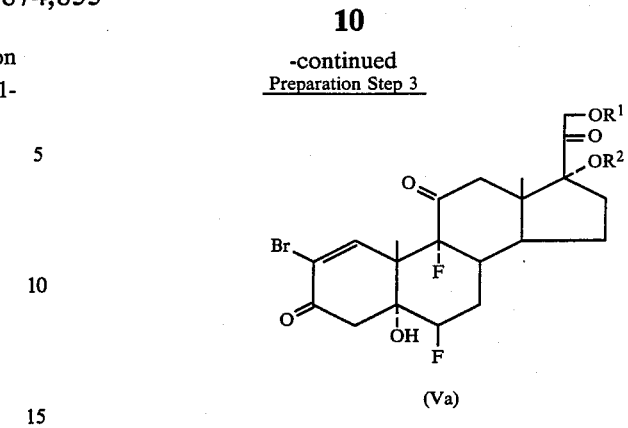

In the above formulae, $R^1$ and $R^2$ have the same meanings as defined above.

The compound (IVa) and bromine are reacted in any organic solvent that does not react with bromine, at a temperature of preferably from $-40°$ C. to $+50°$ C., to form the compound of general formula (Va). The compound (Va) of this invention represents 2-bromo-6β,9α-difluoro-5α,17α,21-trihydroxy-1-pregnen-3,11,20-trione-17,21-diacetate. In the above reaction, a basic compound (e.g., trimethylamine, pyridine and collidine) can be used as reaction assistant. In this case, the reaction can be promoted effectively because hydrobromide obtained as impurity can be captured by the assistant above.

Preparation Step 4

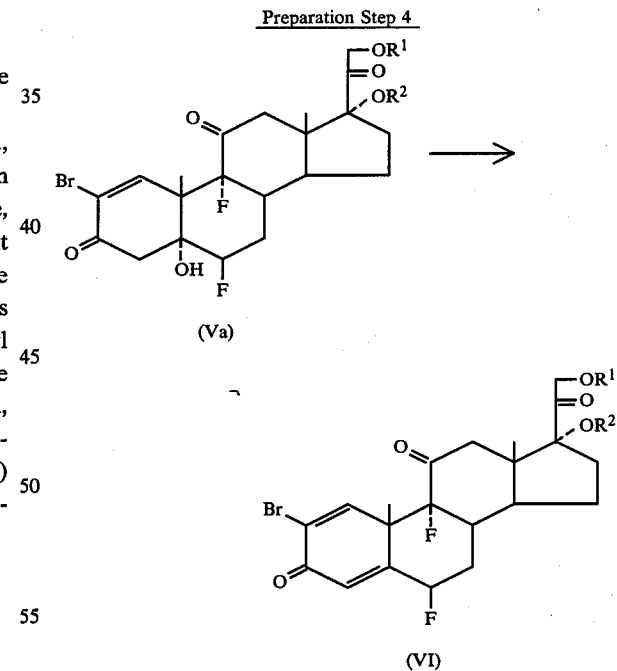

In the above formulae, $R^1$ and $R^2$ have the same meanings as defined above.

The compound (Va) and thionyl chloride are reacted in the presence of a basic compound (e.g., preferably amines such as triethylamine, trimethylamine, pyridine and collidine) in any organic solvent that does not react with thionyl chloride, at a temperature of preferably from $-30°$ C. to $+50°$ C., to form the compound of general formula(VI). Also, the compound (Va) and hydrogen chloride can be reacted in any organic solvent that does not react with hydrogen chloride, at a temperature of preferably from −30° C. to +50° C., to form the compound (VI). The compound (VI) represents 2-bromo-6β,9α-difluoro-17α,21-dihydroxy-1,4-pregnadien-3,11,20-trione-17,21-diacetate.

Preparation Step 5

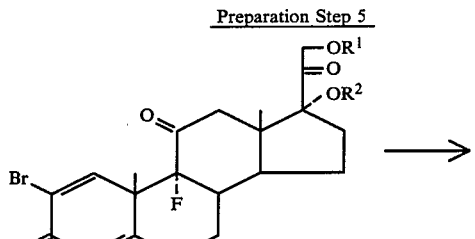

In the above formulae, R[1] and R[2] have the same meanings as defined above.

The compound (VI) and a metal hydride are reacted in an organic solvent (e.g., ethers such as benzene, tetrahydrofuran, dioxane and dimethoxyethane, halogenated hydrocarbons such as methylene chloride, chloroform and dichloroethane, and alcohols such as methanol, ethanol and isopropanol) at a temperature depending on the solvent and the metal hydride, preferably from −80° C. to +60° C., to form the compound of general formula (VII). Examples of the above hydride include metal aluminum hydrides such as lithium aluminum hydride and sodium aluminum bis(2-methoxyethoxy)hydride, metal boron hydrides such as sodium boron hydride and lithium boron hydride and the like. One of the afore-said compounds (VII), the compound (VII) represents 2-bromo-6β,9α-difluoro-11β,17α,21-trihydroxy-1,4-pregnadien-3,20-dione-17,21-diacetate.

Of the compounds of this invention represented by the general formula (I), those compounds in which R[1] and R[2] each represent an acetyl group can be prepared using the compound of the general formula (IIb) as a starting compound by the following process. The starting compound used is 6β,9α-difluoro-5α,11β,17α,21-tetrahydroxypregna-3,20-dione-17,21-diacetate.

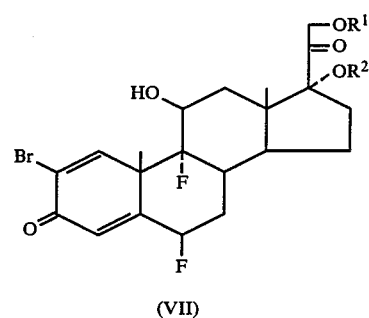

Preparation Step 6

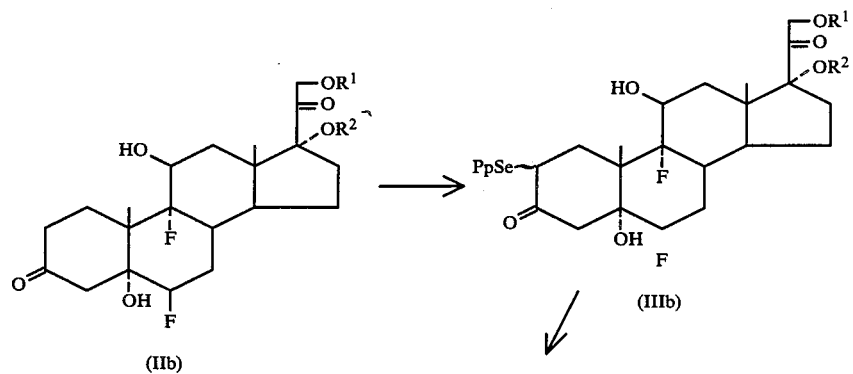

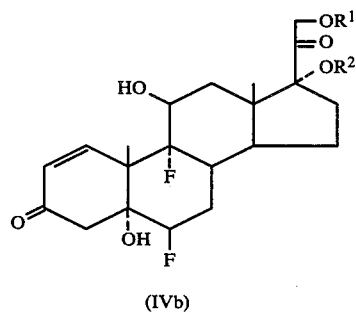

Preparation Step 6

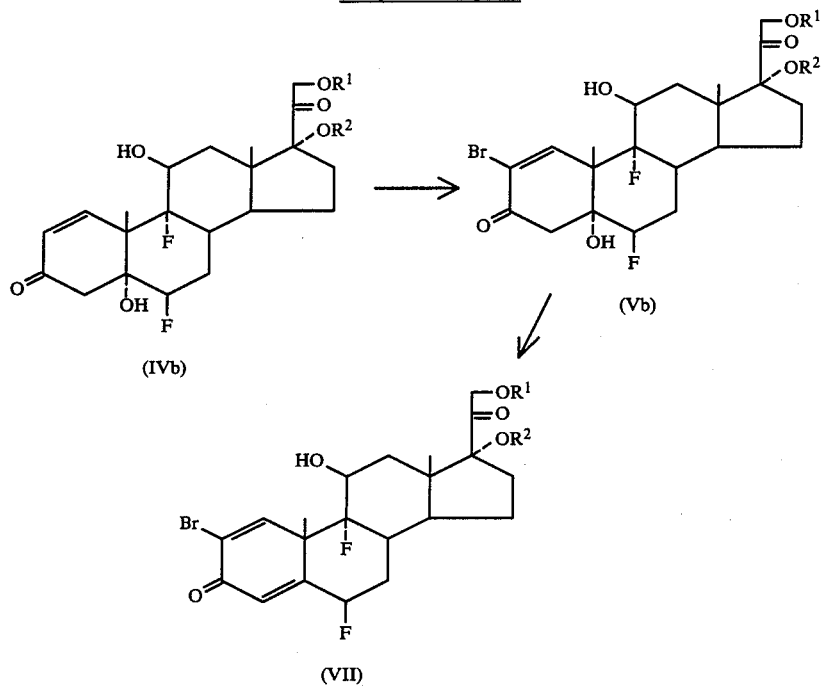

In the above formulae, Pp represents a 2-pyridyl group, and R¹ and R² have the same meanings as defined above.

The compound (IIb) and 2-pyridylselenenyl chloride or 2-pyridylselenenyl bromide are reacted in a solvent (e.g., those used in Preparation Step 1 above) at a temperature depending on the solvent used, preferably from 0° C. to 50° C., to form the compound of the general formula (IIIb). The compound (IIIb) of this invention represents 6β,9α-difluoro-2-(2-pyridylseleno)-5α,11β,17α,21-tetrahydroxypregna-3,20-dione-17,21-diacetate. Phenylselenenyl chloride or phenylselenenyl bromide can be used instead of 2-pyridylselenenyl chloride or 2-pyridylselenenyl bromide as well as Preparation Step 1. In the case, the obtained compound of this invention represents 6β,9α-difluoro-2-phenylseleno-5α,11β,17α,21-tetrahydroxypregna-3,20-dione-17,21-diacetate. The above compound (IIIb) and an oxidizing agent (e.g., those used in Preparation Step 2) are reacted in a solvent (e.g.,those used in Preparation Step 2) at a temperature depending on the oxizing agent and the solvent used, preferably from −50° C. to +30° C., to obtain the compound of the general formula (IVb). The compound (IVb) of this invention represents 6β,9α-difluoro-5α,11β,17α,21-tetrahydroxy-1-pregnen-3,20-dione-17,21-diacetate. The compound (IVb) is further reacted with bromine in any organic solvent that does not react with the bromine, at a temperature of preferably from −40° C. to +50° C., to form the compound of the general formula (Vb). The compound (Vb) of this invention represents 2-bromo-6β,9α-difluoro-5α,11β,-17α,21-tetrahydroxy-1-pregnen-3,20-dione-17, 21-diacetate. In this reaction, a basic compound (e.g., those used in Preparation Step 3) can be used as a reaction assistant. The thus-obtained compound (Vb) and thionyl chloride are reacted in the presence of a basic compound (e.g., those used in Preparation Step 4) in any organic solvent that does not react with thionyl chloride, at a temperature of preferably from −30° C. to +50° C., to obtain the aforedescribed compound (VII). Also, the above compound (Vb) and hydrogen chloride are reacted in any organic solvent that does not react with hydrogen chloride, at the same temperature as above, to form the compound (VII).

Now, with reference to concrete examples this invention will be explained in greater detail below.

EXAMPLE 1

Preparation of 6β,9α-difluoro-2-(2-pyridylseleno)-5α,17α,21-trihydroxypregna-3,11,20-trione-17,21-diacetate (Compound IIIa)

2-pyridylselenenyl chloride (0.58 kg) was added to a solution of 1 kg of 6β,9α-difluoro-5α,17α,21-trihydroxypregna-3,11,20-trione-17,21-diacetate (Compound IIa) in 5 liters of dimethylformamide. To the mixture was added dropwise 35% hydrochloric acid at 30° to 35° C. and the thus-obtained mixture was stirred for 1 hour. After completion of the reaction, the reaction mixture was poured into water (50 liters), and triethylamine (0.61 kg) was added to the mixture. The resulting crystals were collected and recrystallized from methanol to obtain 1.25 kg (yield: 95%, color of crystal: white) of compound (IIIa) having a melting point of 222° to 223.5° C.

IR, cm⁻¹ (KBr): 3550 (νOH);1750,1730,1720,1705(νC=O),1565(νC=C),1230-(νC—O—C)

H¹NMR, δ(CDCl₃): 0.77(3H,s,18CH₃), 1.57(3H,d,J=5.7 Hz,19CH₃), 2.10(3H,s,CH₃CO—), 2.17(3H,s,CH₃CO—), 4.39(1H,dd,J=14.2 Hz, 6.8 Hz, C—2H), 4.50(1H,dm,J=48.5 Hz, C—6H), 4.67(1H,d,J=17.1 Hz, —COCH₂OAc), 4.81(1H,d,J=17.1 Hz, —COCH₂OAc) 7.03(1H,dd,J=8.5 Hz,5.7 Hz, —SeC₅H₄N), 7.34(1H,d,J=8.5 Hz, —SeC₅H₄N), 7.46(1H,dd,J=8.5

Hz, 5.7 Hz, —SeC$_5$H$_4$N), 8.31(1H,d,J=5.7 Hz, —SeC$_5$H$_4$N)

EXAMPLE 2

Preparation of 6$\beta$,9$\alpha$-difluoro-5$\alpha$,17$\alpha$,21-trihydroxy-1-pregnen-3,11,20-trione-17,21-diacetate (Compound IVa)

A solution of 0.655 kg of the compound (IIIa) obtained in EXAMPLE 1 in 6.5 liters of methylene chloride was cooled to 0° C. To the cold solution was added dropwise a 30% hydrogen peroxide solution (0.34 kg). After completion of dropwise addition, the reaction mixture was stirred for 1 hour at 0° C. To the mixture was added 5% aqueous sodium hydrogencarbonate solution, extracted with methylene chloride, and the methylene chloride was removed by evaporation under reduced pressure. The residue was recrystallized from acetone-hexane to obtain 42.3 g (yield: 86%, color of crystal: white) of compound (IVa) having a melting point of 216.5° to 218° C.

IR, cm$^{-1}$ (KBr): 3620($\nu$OH):1720,1680($\nu$-C=O),1230($\nu$C—O—C)

H$^1$NMR,$\delta$(CDCl$_3$) 0.71(3H,s,18CH$_3$), 1.44(3H,d,J=4 Hz,19CH$_3$), 2.14(3H,s,CH$_3$CO—), 2.18(3H,s,CH$_3$CO—), 4.53(1H,dm,J=54 Hz,C—6H), 4.68(1H,d,J=17 Hz,—COCH$_2$OAc), 4.81(1H,d,J=17 Hz,—COCH$_2$OAc) 5.88(1H,d,J=10.5 Hz,C—2H), 7.50(1H,d,J=10.5 Hz,C—1H)

Elemental Analysis (as C$_{25}$H$_{30}$O$_8$F$_2$)
Calculated (%): C,60.48; H,6.09; F,7.65
Found (%): C,60.35; H,6.07; F,7.69

EXAMPLE 3

Preparation of 2-bromo-6$\beta$,9$\alpha$-difluoro-5$\alpha$,17$\alpha$,21-trihydroxy-1-pregnen-3,11,20-trione-17,21-diacetate (Compound Va)

Bromine (0.32 kg) was added to a solution of 1 kg of the compound (IVa) obtained in EXAMPLE 2 in 5 liters of methylene chloride at 25° to 30° C., and the mixture was stirred for 1 hour at the same temperature as above. After stirring, triethylamine was added to the above mixture, stirred further for 30 minutes. To the thus-obtained mixture was added a water, extracted from fraction with methylene chloride, concentrated, and recrystallized from methanol to obtain 1.035 kg (yield: 96%, color of crystal: white) of compound Va) having a melting point of 271.5° C.

IR, cm$^{-1}$ (KBr): 3550($\nu$OH);1730,1690($\nu$-C=O),1590($\nu$C=C),1230($\nu$C—O—C)

H$^1$NMR,$\delta$(CDCl$_3$): 0.77(3H,s,18CH$_3$), 1.58(3H,d,J=4 Hz,19CH$_3$), 2.14(3H,s,CH$_3$CO—), 2.16(3H,s,CH$_3$CO—), 4.54(1H,dm,J=48.5 Hz,C—6H), 4.68(1H,d,J=17 Hz,—COCH$_2$OAc), 4.83(1H,d,J=17 Hz,—COCH$_2$OAc), 7.66(1H,s,C—1H)

Elemental Analysis (as C$_{25}$H$_{29}$O$_8$F$_2$Br)
Calculated(%): C,52.19; H,5.08; Br,13.89; F,6.60
Found (%): C,52.32; H,5.07; Br,13.76; F,6.52

EXAMPLE 4

Preparation of 2-bromo-6$\beta$,9$\alpha$-difluoro-17$\alpha$,21-dihydroxy-1,4-pregnadien-3,11,20-trione-17,21-diacetate (Compound VI)

To a solution of 1 kg of compound (Va) obtained in EXAMPLE 3 above in 5 liters of pyridine was added dropwise a 0.333 liters of thionyl chloride with ice cooling. After completion of dropwise addition, the reaction mixture was stirred for 30 minutes at 30° C. Then, water added to the mixture, which was extracted with methylene chloride, and the extract was concentrated by evaporation. The crude product was purified by column chromatography and crystallized from the fraction (methylene chloride/ethylacetate=15/1) to obtain 0.949 kg (yield: 98%, color of crystal: white) of compound (VI) having a melting point of 262.7° to 263.5° C.

IR, cm$^{-1}$ (KBr): 1750,1740,1676($\nu$C=O),1640,1601($\nu$C=C),1233($\nu$-C—O—C)

H$^1$NMR,$\delta$(CDCl$_3$): 0.78(3H,s,18CH$_3$), 1.63(3H,d,J=2 Hz,19 CH$_3$), 2.07(3H,s,CH$_3$CO—), 2.12(3H,s,CH$_3$CO—), 4.67(1H,d,J=17 Hz,—COCH$_2$OAc), 4.80(1H,d,J=17 Hz,—COCH$_2$OAc), 5.20(1H,dm,J=49 Hz,C—6H), 7.66(1H,s,C—1H)

Elemental Analysis (as C$_{25}$H$_{27}$O$_7$F$_2$Br)
Calculated (%): C,53.87; H,4.88; Br,14.34; F,6.82
Found (%): C,54.01; H,4.77; Br,14.63; F,6.87

EXAMPLE 5

Preparation of 2-bromo-6$\beta$,9$\alpha$-difluoro-11$\beta$,17$\alpha$,21-trihydroxy-1,4-pregnadien-3,20-dione-17,21-diacetate (Compound VII)

A solution of 0.5 kg of compound (VI) obtained in EXAMPLE 4 above in 10 liters of tetrahydrofuran was cooled to −40° C. To the cold solution was added dropwise a solution of 10 g of sodium borohydride in 0.25 liters of tetrahydrofuran, stirred for 4 hours. To the mixture was added dilute sulfuric acid, and the mixture was stirred further for 30 minutes. After completion of stirring, the obtained mixture was extracted from fraction with methylene chloride and water, dried with anhydrous magnesium carbonate, and the solvent in the mixture was removed by evaporation under reduced pressure. The crude crystals were recrystallized from acetone-hexane to obtain 0.45 kg (yield: 90%, color of crystal: white) of compound (VII) having a melting point of 290° C. (decomposed).

EXAMPLE 6

Preparation of 6$\beta$,9$\alpha$-difluoro-2-(2-pyridylseleno)-5$\alpha$,11$\beta$,17$\alpha$,21-tetrahydroxypregna-3,20-dione-17,21-diacetate (Compound IIIb)

Compound (IIIb) (1.24 kg, yield: 95%) was prepared using 1 kg of compound (IIb) as a starting compound in the same manner as the process in EXAMPLE 1. The compound (IIIb) obtained had a melting point of 211° to 212° C. and crystals thereof were white. p IR, cm$^{-1}$ (KBr): 3450 ($\nu$OH);1750,1735,1725($\nu$-C=O),1565($\nu$C=C),1232($\nu$C—O—C)

H$^1$NMR,$\delta$(CDCl$_3$): 0.97(3H,s,18CH$_3$), 1.77(3H,d,J=5.0 Hz,19CH$_3$), 2.09(3H,s,CH$_3$CO—), 2.14(3H,s,CH$_3$CO—), 4.03(1H,d,J=28.5 Hz,C—11H), 4.28(1H,m,C—2H), 4.43(1H,dm,J=45.6 Hz,C—6H), 4.64(1H,d,J=17.1 Hz,—COCH$_2$OAc), 4.90(1H,d,J=17.1 Hz,—COCH$_2$OAc), 7.03(1H,dd,J=8.5 Hz,5.7 Hz, —SeC$_5$H$_4$N), 7.36(1H,d,J=8.5 Hz, —SeC$_5$H$_4$N), 7.46(1H,dd,J=8.5 Hz, 5.7 Hz, —SeC$_5$H$_4$N), 8.37(1H,d,J=5.7 Hz, —SeC$_5$H$_4$N)

EXAMPLE 7

Preparation of
6β,9α-difluoro-5α,11β,17α,21-tetrahydroxy-1-pregnen-3,20-dione-17,21-diacetate (Compound IVb)

Compound (IVb) (0.43 kg, yield: 86%) was prepared using 0.66 kg of compound (IIIb) obtained in EXAMPLE 6 above as a starting compound in the same manner as the process in EXAMPLE 2. The compound (IVb) obtained had a melting point of 197° C. (decomposed) and crystals thereof were white.

IR, cm$^{-1}$ (KBr): 3610,3490($\nu$OH);1750,1735,1710,1675($\nu$C=O),1230($\nu$C—O—C)

H$^1$NMR,δ(CDCl$_3$): 1.02(3H,s,18CH$_3$), 1.61(3H,d,J=4 Hz,19CH$_3$), 2.11(3H,s,CH$_3$CO—), 2.18(3H,s,CH$_3$CO—), 4.53(1H,dm,J=61 Hz,C—6H), 4.68(1H,d,J=17 Hz, —COCH$_2$OAc), 4.95(1H,d,J=17 Hz, —COCH$_2$OAc), 6.07(1H,d,J=10.5 Hz, C—2H), 7.18(1H,d,J=10.5 Hz, C—1H)

Elemental Analysis (as C$_{25}$H$_{32}$O$_8$F$_2$)
Calculated (%): C,60.23; H,6.47; F,7.67
Found (%): C,59.98; H,6.27; F,7.59

EXAMPLE 8

Preparation of
2-bromo-6β,9α-difluoro-5α,11β,17α,21-tetrahydroxy-1-pregnen-3,20-dione-17,21-diacetate (Compound Vb)

Compound (Vb) (0.55 kg, yield:95.5%) was prepared using 0.5 kg of compound (IVb) obtained in EXAMPLE 7 above as a starting compound in the same manner as the process in EXAMPLE 3. The compound (Vb) obtained had a melting point of 216.5° C. (decomposed) and crystals thereof were white.

IR, cm$^{-1}$ (KBr): 3600,3500 ($\nu$OH):1730,1710,1680($\nu$C=O),1590($\nu$C=C),1230($\nu$C—O—C)

H$^1$NMR,δ(CDCl$_3$) 0.88(3H,s, 18CH$_3$), 1.55(3H,d,J=4 Hz, 19CH$_3$), 2.03(3H,s, CH$_3$CO—), 2.10(3H,s, CH$_3$CO—), 4.53(1H,dm,J=54 Hz, C—6H), 4.68(1H,d,J=17 Hz, —COCH$_2$OAc), 4.92(1H,d,J=17 Hz, —COCH$_2$OAc), 7.54(1H,s, C—1H)

Elemental Analysis (as C$_{25}$H$_{31}$O$_8$F$_2$Br)
Calculated (%): C,52.00; H,5.41; Br,13.84; F,6.58
Found (%): C,51.75; H,5.28; Br,13.68; F,6.67

EXAMPLE 9

Preparation of
2-bromo-6β,9α-difluoro-11β,17α,21-trihydroxy-1,4-pregnadien-3,20-dione-17,21-diacetate (Compound VII)

Compound (VII) (0.466 kg, yield: 96%) was prepared using 0.5 kg of compound (Vb) obtained in EXAMPLE 8 above as a starting compound in the same manner as the process in EXAMPLE 4. The compound (VII) obtained had the same characteristics as the compound obtained in EXAMPLE 5 had.

IR, cm$^{-1}$ (KBr): 3520($\nu$OH);1758,1733,1705,1650($\nu$C=O),1590($\nu$C=C),1235($\nu$C—O—C),

H$^1$NMR, δ( CDCl$_3$): 0.91(3H,s, 18CH$_3$), 1.60(3H,d,J=3.4 Hz, 19CH$_3$), 2.01(3H,s,CH$_3$CO—), 2.12(3H,s, CH$_3$CO—), 4.1 - 4.4(1H,broad, C—11H), 4.80(2H,s, —COCH$_2$OAc), 5.39(1H,dm,J=51 Hz, C—6H), 5.63(1H,d,J=6 Hz, C—11OH), 7.85(1H,s, C—1H)

Elemental Analysis (as C$_{25}$H$_{29}$O$_7$F$_2$Br)
Calculated (%): C,53.68; H,5.23; Br,14.28; F,6.79
Found (%): C,53.49; H,5.21; Br,14.53; F,6.75

EXAMPLE 10

Preparation of
6β,9α-difluoro-2-phenylseleno-5β,17α,21-trihydroxy-pregna-3,11,20-trione-17,21-diacetate (Compound IIIa′) (phenylseleno substituted type)

Compound (IIa) (1 kg, yield: 79.3%) was solved in 5 liters of acetonitrile in nitrogen gas stream. To the solution was added 1.25 kg of triethylamine, and further 1 kg of trimethylsilane chloride and 0.1 kg of zinc chloride, and the mixture was stirred for one night at room temperature. After completion of stirring, the reaction mixture was neutralized with a 5% aqueous sodium hydrogencarbonate solution and extracted with methylene chloride, and the methylene chloride layer was concentrated by evaporation, to obtain the 2-trimethylsilyl-ether compound (II′). Without isolating the obtained compound, 1.14 liters of tetrahydrofuran and 0.262 kg of triethylamine were added to the solution containing the ether compound. The resulting solution was cooled at 0° to 5° C., and 0.54 kg of phenylselenenyl bromide was added thereto followed by stirring for 1 hour. After completion of the reaction, the reaction solution was poured into water and extracted with methylene chloride. The extract solution was concentrated, and the concentrate was recrystallized from hexane-ethyl acetate to obtain 1.04 kg (yield: 79.3%, color of crystal: white) of compound (IIIa′) having a melting point of 222.5° to 240° C.

IR, cm$^{-1}$ (KBr): 3650($\nu$OH);1750,1735,1720($\nu$C=O),1580($\nu$C=C),1230($\nu$C—O—C)

H$^1$NMR,δ( CDCl$_3$): 0.71(3H,s, 18CH$_3$), 1.46(3H,d,J=3 Hz, 19CH$_3$), 2.13(3H,s, CH$_3$CO—), 2.16(3H,s, CH$_3$CO—), 4.15(1H,dd,J=12.6 Hz, C—2H), 4.40(1H,dm,J=48 Hz, C—6H), 4.68(1H,d,J=17 Hz, —COCH$_2$OAc), 4.78(1H,d,J=17 Hz, —COCH$_2$OAc), 7.2(3H,m, —SeC$_6$H$_5$), 7.56(2H,m, —SeC$_6$H$_5$)

EXAMPLE 11

Preparation of compound (IVa) using compound (IIIa′) obtained in EXAMPLE 10 above as a starting compound Compound (IVa) (0.422 kg, yield: 85%) was prepared from 0.654 kg of the compound (IIIa′) in the same manner as the process in EXAMPLE 2. The compound (IVa) obtained had the same characteristics as the compound obtained in EXAMPLE 2 had.

EXAMPLE 12

Preparation of
6β,9α-difluoro-2-phenylseleno-5α,11β,17α,21-tetrahydroxypregna-3,20-dione-17,21-diacetate (Compound IIIb′) (phenylseleno substituted type)

Compound (IIIb′) (1.01 kg, yield: 79.4%) was prepared using 1 kg of the compound (IIb) as a starting compound in the same manner as the process in EXAMPLE 10. The compound obtained had a melting point of 199° to 204.5° C.

IR, cm$^{-1}$ (KBr): 3580, 3500($\nu$OH):1755,1735,1725,1710($\nu$C=O),1575($\nu$C=C), 1235($\nu$C—O—C)

H$^1$NMR,δ(CDCl$_3$)(α-SePh form compound): 0.96(3H,s, 18 CH$_3$), 1.59(3H, d,J=5.7 Hz, 19CH$_3$), 2.10(3H,s, CH$_3$CO—), 2.18(3H, s, CH$_3$CO—), 4.22(1H, dd,J=14.3 Hz, C—2H), 4.38(1H, dm,J=48 hz, C—6H), 4.59(1H,d,J=17 Hz, —COCH$_2$OAc), 4.93(1H, d,J=17

Hz, —COCH₂OAc), 7.23-7.36(3H,m,—SeC₆H₅), 7.53-7.63(2H,m, —SeC₆H₅)

H¹NMR,δ(CDCl₃)(β-SePhg form compound) 1.00(3H,s, 18CH₃), 1.59(3H,d,J=5.7 Hz, 19CH₃), 2.10(3H,s, CH₃CO—), 2.18(3H,s, CH₃CO—), 4.22(1H,d,J=8.6 Hz, C—2H), 4.38(1H,dm,J=48 Hz, C—6H), 4.64(1H,d,J=17 Hz, —COCH₂OAc), 4.96(1H,d,J=17 Hz, —COCH₂OAc), 7.23-7.36(3H,m, —SeC₆H₅), 7.53-7.63(3H,m, —SeC₆H₅)

EXAMPLE 13

Preparation of compound (IVb) using compound (IIIb') obtained in EXAMPLE 12 above as a starting compound Compound (IVb) (0.43 kg, yield: 85.7%) was prepared from 0.66 kg of compound (IIIb') in the same manner as the process in EXAMPLE 2. The compound obtained had the same characteristics as the compound obtained in EXAMPLE 7 had.

What is claimed is:

1. A steroid compound represented by general formula

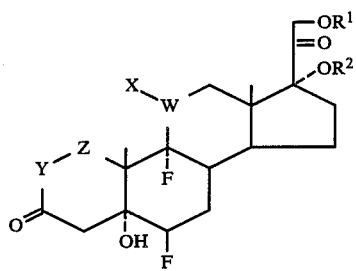
(I)

wherein X and W together as >W—X represent a carbonyl group (>C=O) or a hydroxymethylene group (>CH(OH)), the hydroxy moiety of the hydroxymethylene group being of β-arrangement, and OR¹ and OR² independently represent an ester residue, and Y and Z together as —Y—Z— represent a —(PpSe)-CH—CH₂— group where Pp represent a phenyl group or a 2-pyridyl group, or Y and Z each represent an ethenylene group or a 1-bromoethenylene group.

2. The steroid compound as claimed in claim 1, which is represented by general formula (III)

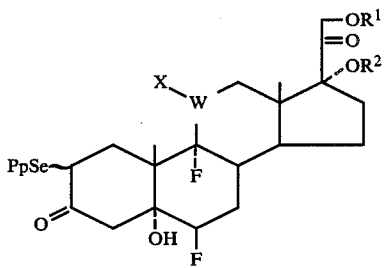
(III)

wherein X, W, OR¹ and OR² have the same meanings as defined above, and wherein Pp represents a 2-pyridyl group.

3. The steroid compound as claimed in claim 2, wherein >W—X represents >C=O.

4. The steroid compound as claimed in claim 2, wherein >W—X represents >CH(OH), the hydroxy moiety of the hydroxymethylene group being of β-arrangement.

5. The steroid compound as claimed in claim 1, which is represented by general formula (III)

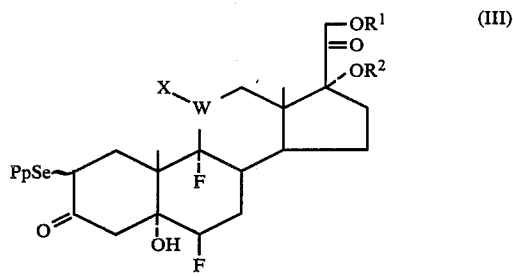
(III)

wherein X, W, OR¹ and OR² have the same meanings as defined above, and wherein Pp represents a phenyl group.

6. The steroid compound as claimed in claim 5, wherein >W—X represents >C=O.

7. The steroid compound as claimed in claim 5, wherein >W—X represents >CH(OH), the hydroxy moiety of the hydroxymethylene group being of β-arrangement.

8. The steroid compound as claimed in claim 1, which is represented by general formula (V)

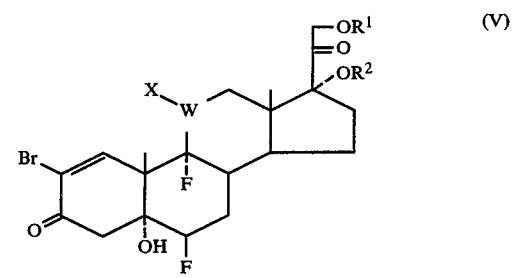
(V)

wherein X, W, OR¹ and OR² have the same meaning as defined above.

9. The steroid compound as claimed in claim 8, wherein >W—X represents >C=O.

10. The steroid compound as claimed in claim 8, wherein >W—X represents >CH(OH), the hydroxy moiety of the hydroxymethylene group being of β-arrangement.

11. The steroid compound as claimed in claim 1, which is represented by general formula (IV)

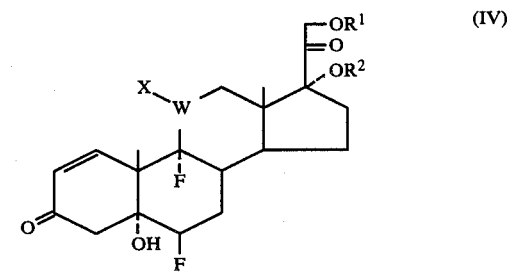
(IV)

wherein X, W, OR¹ and OR² have the same meanings as defined above.

12. The steroid compound as claimed in claim 11 wherein >W—X represents >C=O.

13. The steroid compound as claimed in claim 11, wherein >W—X represents CH(OH), the hydroxy moiety of the hydroxymethylene group being of β-arrangement.

14. A process of preparing steroid compounds represented by the general formula (III)

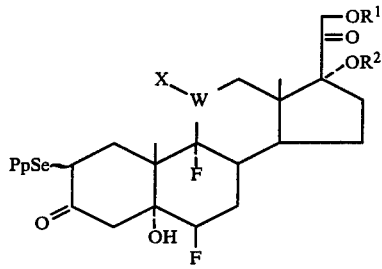 (III)

wherein X and W together as >W—X represent a carbonyl group (>C=O) or a hydroxymethylene group (>CH(OH)), the hydroxy moiety of the hydroxymethylene group being of β-arrangement, and $OR^1$ and $OR^2$ independently represent an ester residue, and Pp represents a phenyl group or a 2-pyridyl group, which comprises reacting 6β,9α-difluoro-5α,17α,21-trihydroxypregna-3,11,20-trione-17,21-di-esters or 6β,9α-difluoro-5α,11β,17α,21-tetrahydroxypregna-3,20-dione-17,21-diesters represented by the general formula (II)

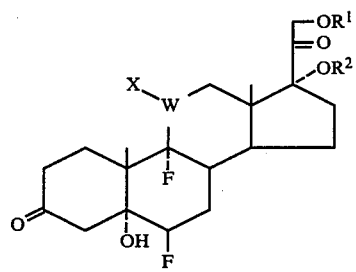 (II)

wherein X, W, $OR^1$ and $OR^2$ have the same meanings as defined above, as starting compound with an organic selenenyl halide selected from the group consisting of 2-pyridylselenenyl chloride, 2-pyridylselenenyl bromide, phenylselenenyl chloride and phenylseleneny bromide.

15. A process of preparing 2-bromo-6β,9α-difluoro-11β,17α, 21-trihydroxy-1,4-pregnadien-3,20-dione-17,21-diester represented by general formula(VII)

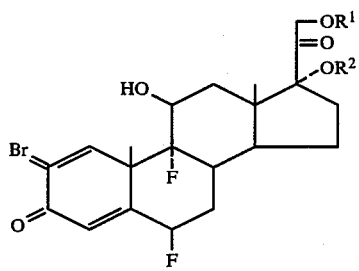 (VII)

wherein $OR^1$ and $OR^2$ independently represent an ester residue wherein one or more compounds represented by general formula (I)

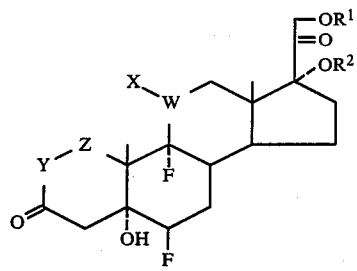 (I)

wherein X and W together as >W—X represent a carbonyl group (>C=O) or a hydroxymethylene group (>CH(OH)), the hydroxy moiety of the hydroxymethylene group being of β-arrangement, and $OR^1$ and $OR^2$ independently represent an ester residue, and Y and Z together as —Y—Z— represent a —(PpSe)-CH—$CH_2$— group where Pp represent a phenyl group or a 2-pyridyl group, or Y and Z each represent an ethenylene group or a 1-bromoethenylene group, are involve in the reaction as reaction intermediate.

16. The process as claimed in claim 15, comprising reacting with hydrogen chloride, or with thionyl chloride in the presence of a basic substance, a compound represented by general formula (V)

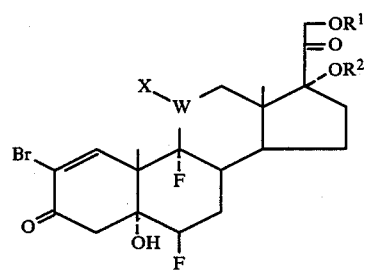 (V)

wherein X, W, $OR^1$ and $OR^2$ have the same meaning as defined above, and optionally reducing the resulting compound with a reducing agent when >W—X represents a carbonyl group.

17. The process as claimed in claim 15, comprising
(a) reacting a steroid compound represented by the general formula (II)

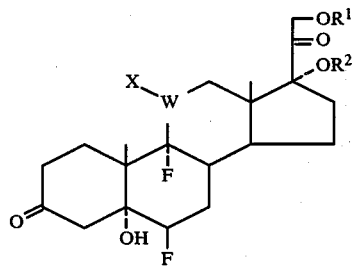 (II)

wherein X, W, $OR^1$ and $OR^2$ have the same meanings as defined above, with an organic selenenyl halide selected from the group consisting of 2-pyridylselenenyl chloride, 2-pyridylselenenyl bromide, phenylselenenyl chloride and phenylselenenyl bromide, to obtain a compound represented by the general formula (III)

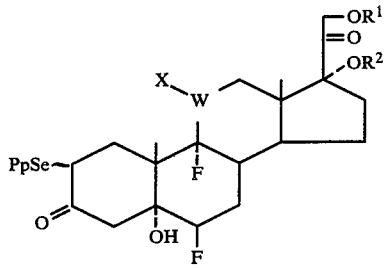

(III)

wherein X, W, OR¹ and OR² have the same meanings as defined above, (b) oxidizing the compound represented by the general formula (III) to obtain a compound represented by the general formula (IV)

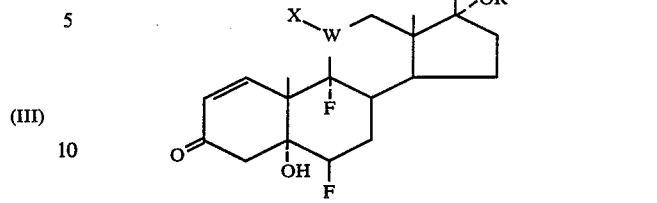

wherein X, W, OR¹ and OR² have the same meanings as defined above, (c) brominating the compound represented by the general formula (IV) with bromine to obtain a compound represented by the general formula (V)

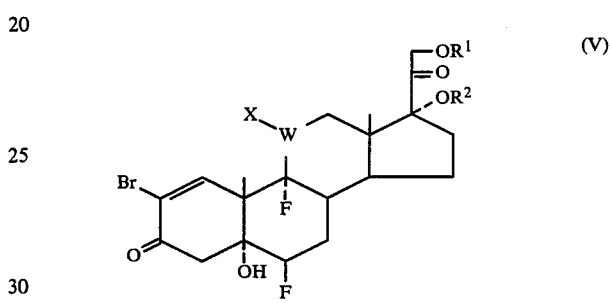

wherein X, W, OR¹ and OR² have the same meanings as defined above, and (d) reacting the compound represented by the general formula (V) with hydrogen chloride, or with thionyl chloride in the presence of a basic substance, and optionally reducing the resulting compound with a reducing agent when >W—X represents >C=O.

* * * * *